United States Patent [19]

Theeuwes et al.

[11] Patent Number: 4,655,766

[45] Date of Patent: Apr. 7, 1987

[54] FLUID IMBIBING PUMP WITH SELF-REGULATING SKIN PATCH

[75] Inventors: Felix Theeuwes; James B. Eckenhoff, both of Los Altos, Calif.

[73] Assignee: ALZA Corporation, Palo Alto, Calif.

[21] Appl. No.: 853,262

[22] Filed: Apr. 17, 1986

Related U.S. Application Data

[63] Continuation-in-part of Ser. No. 761,740, Aug. 1, 1985, abandoned, which is a continuation of Ser. No. 450,887, Dec. 20, 1982, abandoned.

[51] Int. Cl.$^4$ ............................................. A61K 9/00
[52] U.S. Cl. ..................................... 604/896; 604/897
[58] Field of Search .......... 604/93, 131, 140, 304–309, 604/890–897; 128/155, 156; 424/15–22; 427/2; 428/304.4–311.1; 222/92, 95, 386.5, 193, 389, 130

[56] References Cited

U.S. PATENT DOCUMENTS

| | | | |
|---|---|---|---|
| 2,561,071 | 7/1951 | Prisk | 604/896 |
| 3,053,255 | 9/1962 | Meyer | 604/307 |
| 3,814,097 | 6/1974 | Ganderton et al. | 604/304 |
| 4,014,334 | 3/1977 | Theeuwes et al. | 604/896 |
| 4,077,407 | 3/1978 | Theeuwes | 604/896 |
| 4,350,271 | 9/1982 | Eckenhoff | 222/386.5 |
| 4,460,370 | 7/1984 | Allison et al. | 604/897 |

Primary Examiner—Stephen C. Pellegrino
Assistant Examiner—Gene B. Kartchner
Attorney, Agent, or Firm—Steven F. Stone; Edward L. Mandell; Paul L. Sabatine

[57] ABSTRACT

A medical device comprising a fluid imbibing, self-regulating, skin patch drug delivery system is disclosed which includes a fluid imbibing, preferably osmotic, pump comprising a reservoir for a drug or, drug formulation or other fluid to be dispensed to the skin, 10 at least one wall of the reservoir comprising a fluid permeable membrane which is permeable to an external activating fluid. The external fluid is imbibed through the membrane at a predetermined rate thereby causing the drug to be pumped through one or more passages provided in the reservoir structure and 15 into contact with the skin. The device includes an impermeable exterior wall member which covers and extends outwardly from the fluid imbibing pump terminating in an edge portion adapted to be secured, as by adhesion, to the skin. The exterior wall member, when attached to the skin surface, defines the area of skin which is available for distribution of the drug formulation pumped from the reservoir which is large enough, at the lowest anticipated skin permeation, to deliver the drug to the body at the rate at which it is discharged from the fluid imbibing pump in the preferred embodiments the fluid permeable membrane is a semipermeable membrane, impermeable to the drug or drug formulation.

39 Claims, 6 Drawing Figures

FLUID IMBIBING PUMP WITH SELF-REGULATING SKIN PATCH

RELATED PATENT APPLICATIONS

This application is a continuation-in-part of application Ser. No. 761,740 filed Aug. 1, 1985, now abandoned and which was a continuation of application Ser. No. 450,887 filed Dec. 20, 1982 now abandoned.

FIELD OF THE INVENTION

This invention relates to medical devices for delivering drugs, and more particularly to a self-regulating skin patch incorporating a fluid imbibing pump drug delivery device which includes membrane means adapted to control the rate of administration of the drug to the skin, and an impermeable exterior wall member extending over the pump and adapted to be attached to the skin to define an area sufficiently large so that the rate of transdermal delivery of a drug formulation is determined by the rate of fluid discharge from the pump.

BACKGROUND OF THE INVENTION

Transdermal drug delivery systems are known and have achieved generally widespread acceptance in providing systemic therapy for certain human conditions. (As used herein the term "drug" is intended to be interpreted in its broadest sense to include any material that is to be delivered into the body to provide a desired, usually beneficial, effect.) Typically, these transdermal drug delivery systems are diffusional in nature and their applications have been somewhat limited in that the rate of administration of drug to the skin designed into the delivery systems must be restrained (controlled) to take into account the skin's permeability to the drug and therapeutic plasma level, and the marked intra and inter-individual differences in skin permeability. That is to say, these system's rate-limiting resistance to drug transport must be selected to be considerably higher than the resistance of the skin to drug absorption for controlled, systemic therapy. Conversely stated, to control the rate of drug absorption from diffusional dosage form designs the flux of drug from the system must be considerably lower than the limiting absorption flux of the skin.

Among such diffusional dosage systems, or bandages for the transdermal administration of drugs are those described in U.S. Pat. Nos. 3,797,494 and 4,031,894, which collectively disclose bandages in the form of laminates including a backing, a drug reservoir, a microporous membrane and a contact adhesive layer. The microporous membrane in such devices acts to limit the rate of drug administration.

Osmotic systems useful in the topical administration of drugs are also known. Perhaps the systems which are most relevant to this invention are those shown in U.S. Pat. Nos. 4,014,334 and 4,077,407, each of which discloses an osmotic device in which an active agent, or drug, is contained within a compartment defined by a wall formed from a material permeable to an external fluid but impermeable to the active agent contained within the compartment. An aperture in the wall communicates with the chamber to permit dispensing of the active agent which exhibits an osmotic pressure gradient across the wall against the external fluid, or which is mixed with an agent exhibiting such pressure gradient when used for the topical application of ARC 695 systems do not achieve the relatively high transdermal delivery rates envisioned through use of the present invention.

OBJECTS OF THE INVENTION

It is the primary object of the present invention to provide an improved delivery system for transdermal delivery of an active agent over a prolonged period at a controlled, substantially uniform rate approximating the skin's rate-limiting flux.

Another object of the invention is to provide an device delivery system which when applied to the skin defines an area of transdermal application in which the active agent is dispensed to assume its own surface area for absorption into the skin at a relatively high rate.

Another object of the invention is to provide a drug delivery device which is self-regulating in its delivery rate.

Another object of the invention is to provide such device which may be used to deliver a wide variety of active agents, including agents in salt form, skin permeation enhancers agents in oil, water, or other solutions, and formulations of various compatible agents.

Another object of the invention is to provide such an osmotic device including a chamber for containing a quantity of the active agent, with one wall of the chamber being defined by a material permeable to an external fluid and substantially impermeable to the agent, for imbibing external fluid into the chamber and including means for dispersing solution of the fluid and agent dispensed from the osmotic device over an area of the skin sufficient to enable permeation of the active agent into the skin at the rate at which it is pumped from the chamber. Another object of the invention is to provide a transdermal delivery device wherein the rate of application of the active agent is dependent on the rate at which liquid is imbibed into the chamber and substantially independent of the permeability of the skin.

Another object is to provide an osmotic drug delivery system for transdermal administration of drugs wherein the drug absorption rate occurs at the skin's rate-limiting flux but at a controlled rate.

Another object of the invention is to provide delivery system for providing either a single, delayed pulse, or a delayed onset of continuous administration of drug to the skin.

SUMMARY OF THE INVENTION

The foregoing and other objects and advantages are achieved in accordance with the present invention wherein a self-regulating skin patch is employed in conjunction with a fluid imbibing pump to control transfer of drugs from the device to the skin at relatively high rates. The system pumps its contained drug formulation independent of drug boundary conditions, self-selects needed skin surface for drug delivery and allows higher fluxes through the skin at a controlled rate than previously could be obtained.

As used herein the term "fluid imbibing pump" encompasses that class of devices which deliver their contents, upon exposure to an external fluid, at a rate corresponding to the rate at which the external fluid is imbibed into the pump. These devices are known to the art and operate on diffusional and osmotic principals and are disclosed for example in U.S. Pat. Nos. 435,027, 4,327,725, 4,210,139, 4,203,442, 4,203,440, 4,111,203, 4,111,202, 4,016,880, 3,995,631, 3,987,790, 3,916,899, 3,845,770 and 3,760,984 which are incorporated herein by reference. While various types of fluid imbibing pumps can be used herein the preferred embodiments utilize the osmotically driven versions and the invention will be described with respect thereto for purposes of description 20 not limitation.

The typical osmotic device includes a semipermeable membrane, i.e., a membrane permeable to an external fluid but impermeable to the solute or the pharmacologically active agent or drug to be dispensed, and an impermeable exterior wall member extending over the osmotic device and adapted to be attached, as by adhesive, to the skin to define an area of skin to which the drug may be administered from the device. As the external fluid is imbibed through the semipermeable membrane, the drug solution or formulation is discharged at a controlled rate of delivery through an opening in the membrane or through an opening in a suitable housing structure for the osmotic device, to be dispersed over the skin area defined by the system's external wall covering, to achieve the desired absorption at 5 the skin's rate-limiting flux. The semipermeable membrane is selected to control delivery rate independent of skin permeability.

BRIEF DESCRIPTION OF THE DRAWINGS

Other features and advantages of the invention will be apparent from the detailed description contained herein below, taken in conjunction with the drawings, in which.

DETAILED DESCRIPTION OF THE INVENTION

Figure 1:
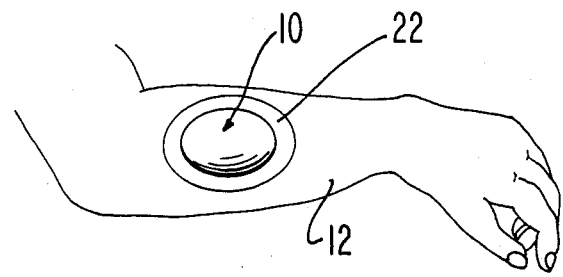
FIG. 1 is an isometric view showing a self-regulating skin patch according to the invention attached to a human arm.

For many drugs it is important, or critical, that accurate and predictable control of the time to onset and/or rate of drug administration is maintained. For transdermal application of such drugs, the effect of differences in skin permeability must be overcome, or compensated, if the necessary control of the drug input rate is to be obtained. The desired controlled rate of delivery is achieved in accordance with the present invention by use of the self-regulating skin patch drug delivery system identified generally in the drawings by the reference numeral 10, and incorporating fluid imbibing pump, for controlled delivery of the drug. The skin patch 10 is illustrated in FIG. 1 as being attached, as by adhesive, directly to the skin on the forearm 12 for transdermal delivery of a drug formulation 15 to the person wearing the skin patch.

Figure 2:
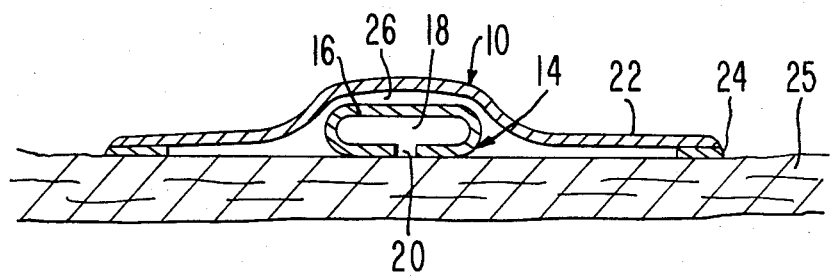
FIG. 2 is an enlarged sectional view of an embodiment of a skin patch shown in FIG. 1.

The simplest form of the invention illustrated in the drawings is shown in FIG. 2 wherein the skin patch 10 utilizes an elementary osmotic pump 14 defined by a wall 16 surrounding compartment 18 dimensioned to contain the desired quantity of a drug formulation and to deliver the drug to the skin at a predetermined rate. An aperture 20 is formed in wall 16 to provide an outlet for drug formulation discharged by the osmotic pump 14. In use, the drug formulation contained in compartment 18 may be water soluble and will exhibit an osmotic pressure gradient across wall 16 against water extracted by the device from the skin of the person wearing the device, or the formulation may contain a mixture of agents at least one of which will exhibit such osmotic pressure gradient. Further, the formulation may contain permeation enhancers, cytoprotective agents, stabilizing agents or other additives as may be necessary for any particular drug system.

At least the portion of the wall 16 which will normal be in contact with the skin when the device is in use is made of a semipermeable material which is permeable to the passage of body fluids (water) but substantially impermeable to the 10 passage of the drug formulation and other agents within the chamber 18.

A wall 22 formed of a material which is substantially impermeable both to formulation contained in compartment 18 and to body fluids extends over and projects outwardly from the osmotic pump device 14 and preferably has a band 24 of adhesive material coated on its peripheral edge portion for securely but releasably attaching the system directly to the skin of the person wearing the device. The adhesive may contain dispersed drug and other additives if desired to provide for an initial pulse delivery of drug.

The preferred configuration of wall 22 is substantially circular or oval in plan view, with the adhesively coated peripheral edge portion extending outwardly a substantial distance from the osmotic pump device 14. The passage way 20 is formed in wall 16 of the osmotic device on the surface thereof opposite to the wall 22. Preferably the walls 16 and 22 are securely attached, as at 26, by suitable means such as an adhesive or by heat bonding. Wall 22 is preferably contoured to conform closely to the skin surface and cooperate therewith to confine and distribute drug formulation dispersed from chamber 18.

Prior to use, the osmotic delivery system may also include a strippable, protective layer (not shown) that adheres to the adhesive edge coating on wall 22. Just prior to use, the layer is peeled away from wall 22 and discarded. It may be made from any conventional material, such as polymers, with the provision that such material is, or is made to be, strippable through the use of slip agents, such as by siliconizing.

In operation in the environment of use, the skin patch 10 of FIG. 2 is attached directly to the skin as illustrated in FIG. 1. The formulation contained in compartment 18 has a water soluble component causing water to be imbibed into the compartment from the skin in a tendency toward osmotic equilibrium. The rate of dissolution is controlled by the water permeability of the semipermeable wall or membrane 16 in contact with the skin and the osmotic pressure gradient across the wall 16. Since the formulation contains sufficient amounts of the water soluble component to maintain the solution within the chamber at the saturation level during substantially the entire delivery period, the osmotic pressure differential and the concentration of active agent in the fluid to be dispensed remain substantially constant. Thus water is continuously imbibed at a controlled rate to continuously form a solution of the formulation in the chamber which is then pumped through outlet passage 20 at a controlled and continuous rate substantially equal to the rate at which body fluid is imbibed into chamber 18. As the solution is pumped through outlet 20, it is free to spread over the surface of the skin layer 25 for transdermal absorption. The surface area of skin covered by the impermeable wall 22 is selected to be large enough to permit adequate drug delivery through the skin at the lowest anticipated skin permeability. Thus, the fluid discharge rate through opening 20 will determine the rate of drug absorption through the skin since the drug solution will extend to cover the necessary area to establish equilibrium between the rate delivered to the skin and that delivered through the skin into body tissues.

Figure 3:
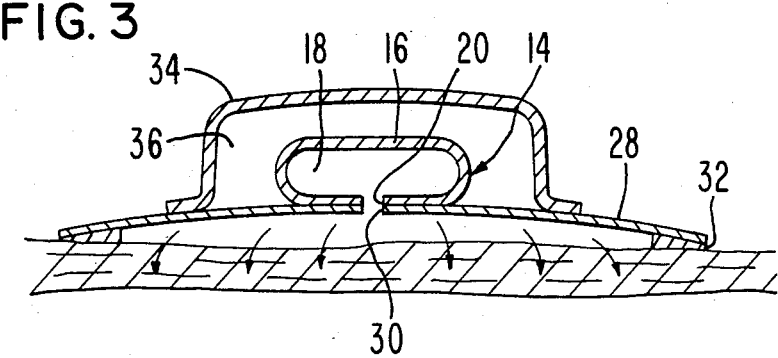
FIG. 3 is a view similar to FIG. 2 and showing an alternate embodiment of the invention.

FIG. 3 schematically depicts a further embodiment of the invention which is particularly well adapted for dispensing a formulation at a relatively high rate. In this embodiment, the fluid imbibing pump 14 may be identical to that described above, and identical reference numerals are used to designate corresponding parts of this device. In this embodiment, the wall portion 16 adjacent outlet opening 20 is secured, as by suitable adhesive or heat sealing, to an impermeable wall 28 having a central opening 30 in alignment with outlet opening 20. Preferably an adhesive material is applied in a continuous band 32 around the peripheral edge of impermeable wall 28 on the surface thereof opposite to that to which the osmotic pump device 14 is attached. A second impermeable wall 34 extends over osmotic pump device 14 and is secured to impermeable wall 28 and cooperates therewith to define a fluid chamber 36 for containing a suitable fluid such as water which may be injected, as by a hypodermic needle or other suitable device, to activate the skin patch.

In operation of the embodiment shown in FIG. 3, the adhesive band 32 on impermeable wall 28 is attached to the skin as described above with reference to FIG. 2. Water or other suitable fluid from fluid chamber 36 penetrates semi-permeable wall 16 to form a solution with the drug formulation contained in chamber 18 and is pumped through openings 20 and 30 to be absorbed transdermally. Again, the area of skin available for contact by the fluid beneath wall 28, as defined by adhesive band 32, is sufficiently large to enable the formulation solution pumped from the device to spread over the necessary area so that skin permeability is not controlling of rate; instead, the rate of permeation of the fluid from chamber 36 through wall 16 controls the dosage rate. In FIG. 3 a substantial space is shown between wall 28 and the surface of skin layer 25 for clarity of illustration; however, in use, the wall 28 would normally be in close proximity to or in direct contact with the skin surface.

The embodiment of FIG. 4 again employs an osmotic fluid imbibing pump 14 as described with reference to FIG. 2; however, in this embodiment, the discharge outlet 20 in the wall 16 is oriented on the side of the device opposite that which is in contact with the skin. The osmotic pump device is surrounded by a short, rigid or semirigid wall member 38 of substantially impermeable material, and preferably the wall 16 is secured, as at 40, to the wall 38 by suitable means such as adhesive. A wall 42 of impermeable material is positioned over osmotic pump 14 and wall 38, and extends outwardly there from for attachment to the skin, as by a peripheral adhesive band 44. The wall 38 is contoured to extend in spaced relation to the skin in the area inboard of the adhesive band 44 and in spaced relation to the top edge 46 of wall 38 to provide a fluid flow passage there between. An open pore foam material 48 fills the space between osmotic pump device 14 and the impermeable wall 42 within the area defined by wall 38, and also fills the area outside wall 38 from the plane of the bottom edge of wall 38, i.e., the plane normally in contact with the skin when the device is in use.

Figure 4:
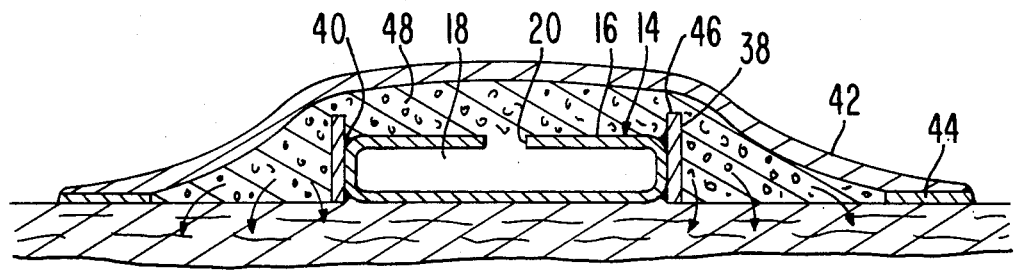
FIG. 4 is a sectional view of a further embodiment of the invention.

In use of the embodiment shown in FIG. 4, external fluid from the skin is imbibed into formulation chamber 18 through the semipermeable wall 6 to form a drug solution which is then osmotically pumped through the outlet opening 20 into the open pore foam body 48. The foam body may be devoid of the formulation prior to use in which there will be delay in start-up. Alternatively the foam body may be substantially saturated with a solution or suspension of the formulation before the device is placed in use so that, as soon as the system is applied to the skin, transdermal application of the drug commences. In addition permeation enhancers such as dimethyl sufoxide (DMSO), ethanol, dimethyl lauramide or polyethylene glycol monolaurate (PEGML); and cytoprotective 5 agents such as prostaglandins or other additives for example, may be impregnated in the foam prior to use. As water is imbibed into chamber 18 to form additional solution which is pumped through outlet opening 20, formulation transferred from foam body 48 is replaced by the osmotic pumping action and a substantially continuous application of drug takes place. Again, the skin area in contact with the foam material is large enough so that skin permeability is not a limiting factor in drug delivery.

Figure 5:
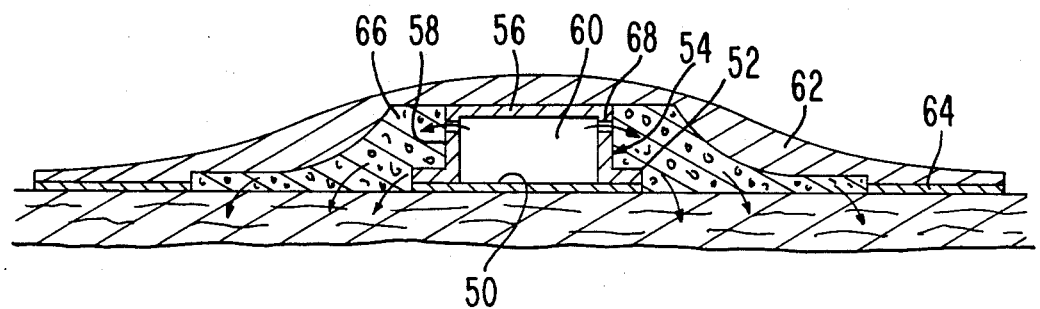
FIG. 5 is a sectional view of yet another embodiment of the invention.

The embodiment shown in FIG. 5 is quite similar in operation to that just described with reference to FIG. 4, and differs there from primarily in the construction of the osmotic pumping device employed. In this embodiment, a semipermeable membrane, or wall 50 extends over and is firmly attached to the outer surface of an outwardly directed flange 52 on the open end of a generally cylindrical formulation cup 54 having an end wall 56 and sidewall 58 defining a closed formulation chamber 60. An impermeable outer wall member 62 extends over cup 54 and is preferably secured to the end wall 56 as by adhesive bonding. Again, a peripheral band of adhesive material 64 is preferably provided on outer wall 62 to attach the system to the surface of skin layer 25. A body of open pore foam material 66 fills the cavity between outer wall 58 and the inner surface of impermeable wall 62, and one or more outlet openings 68 are provided in the cylindrical wall 58 to permit a solution of drug formulation to be pumped from chamber 56.

Figure 6:
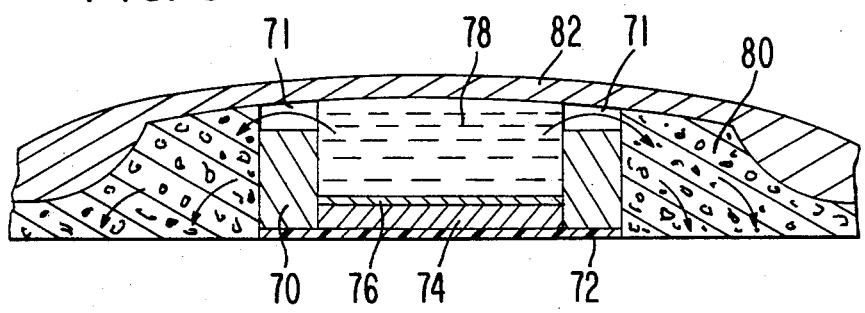
FIG. 6 is an enlarged sectional view schematically showing a further embodiment of the invention.

Referring now to FIG. 6, a modification of the embodiments shown in FIGS. 4 and 5 is schematically illustrated in which a short cylindrical structural member 70 defines reservoir housing with outlets 71, with a semipermeable 10 membrane 72 extending over one end of the housing. A thin layer of an osmotic agent 74 is positioned adjacent membrane 72 within the housing 70, and a partition wall 76 that is impermeable to the outside fluid and impermeable to drug formulation 15 extends over the osmotic agent separating the agent from the drug containing reservoir 78. The impermeable wall may be either a highly flexible, fluid impermeable material sealed to housing 70 or a piston in sliding, fluid, sealing relationship with housing 70. A pad 80 of open pore foam material surrounds the drug formulation 78 contained in the reservoir compartment formed within housing 70 and provides a conduit to the skin for the drug formulation pumped from outlet 71. An impermable membrane or wall 82 extends over the surface of foam pad on the side thereof opposite membrane 72.

Operation of this embodiment is substantially identical to that described above with regard to FIGS. 4 and 30 5, with the exception that the osmotic agent is not mixed with the drug formulation but is instead included within a separate chamber in the reservoir housing adjacent membrane 72 to promote the transfer of fluid through membrane. When fluid is imbibed through membrane 78 the partition 76 is distended or if in the form of a piston, driven, into reservoir 78 to drive out the fluid drug formulation into the pad 80 for absorption. Fluid drug formulation 78 can be a solution, suspension, semisolid or solid that converts to a flowable liquid or gel at body temperature. A diffusional rather than osmotic fluid embibing pump can be constructed simply by using a material of known water permeability for membrane 72 and a hydrophillic water swellable gel for material 74. In an another alternate embodiment partition 76 and osmotic agent 74 may be combined into one gel layer, having osmotic imbibition properties and being capable of excluding the drug formulation 78 as is known to the fluid imbibing pump art.

The semipermeable material employed in the osmotic pump devices of the invention may be selected from known materials which are compatible with the formulation employed. In this respect, various suitable materials are disclosed in the above mentioned U.S. Pat. Nos. 4,014,334 and 4,077,407, the disclosures of which are incorporated herein by reference. Also, suitable resilient or flexible impermeable synthetic resin materials may be selected from the known art for use in construction of the outer wall members of the skin patch, and suitable semirigid or rigid materials may be selected for wall members surrounding or forming flow barriers within the internal structure of the drug delivery system where such internal structure is employed. In order to design a skin patch according to this invention, the minimum anticipated rate at which water is 5 available for imbibition into the patch and the rate of permeation of drug through the skin are determined. Our tests on human subjects have shown that the average rate of water absorption encountered was never less than approximately 0.5 mg/hour/cm$^2$. A membrane whose overall resistance to water permeation is $2.6 \times 10^5$ hr atm/cm$^2$ is adequate to provide rate control of the imbibing process at such water absorption rates.

The permeability of skin to various drugs are known as shown, for example, in Michaels et al, Drug Permeation through Human Skin: Theory and In Vitro Experimental Measurements; Am. Ind. Chem. Eng.2(5), 985-996, Sept., (1975) or can be determined experimentally by direct measurements of absorption rates from controlled samples as is known to the art. With these values determined one can select the area of the water permeable membrane to provide the desired steady state drug delivery rate and select the area confined within the patch to be sufficient to absorb all drug delivered at the lowest anticipated drug permeability. This permits drug to be dispersed to the skin at a controlled rate, above the rate limiting absorption rate for the drug through the skin. As drug in a fluid medium is dispensed it will spread over the skin within the patch to seek the area necessary for any particular subjects skin permeability for the drug. The following example describe skin patches according to this invention for delivering representative drugs.

EXAMPLE 1

A drug formulation is made from 10% clonidine, 60% light mineral oil, 2.4% colloidal silicon dioxide, and 27.6% polyisobutylene (35000). An osmotic skin patch of the type shown in FIG. 6 is made as follows.

DENSIL transfer adhesive is applied to the bottom face of a 2 cm radius disc of ELVAX 210. The disc of ELVAX, thickness of 0.1 cm, is die cut with 1.8 cm radius punch to form an annular drug reservoir. An annulus of open pore, semirigid foam material having a 2.5 cm outside diameter and 2 cm inside diameter is formed having 0.15 cm thickness. The ELVAX 210 drug reservoir is inserted inside the open pore foam material annulus until the adhesive side of the drug reservoir is flush with the bottom of the foam material. A 2 cm radius disc of cellulose acetate butyrate 500-1 is positioned concentric with the drug reservoir and affixed to the adhesive side of the drug reservoir. A 0.02 cm thick osmoagent wafer of powdered potassium sulfate in a hydrophilic binder matrix is formed and die cut to 1.8 cm radius and placed inside the drug reservoir on top of the membrane disc. A partition form from 0.025 cm wafer of POLYOX ® is placed on top of the osmoagent and 500 mg of the clonidine drug formulation is dispensed into the drug reservoir which is subsequently sealed with a 2.5 cm radius disc of MEDPAR ® backing material. The MEDPAR ® formed a contact seal over the drug reservoir and the open pore, foam material annulus. A Microfoam adhesive overlay was used for securing the system onto skin. If two identical systems are fabricated and tested in vivo on two 5 subjects with different skin resistances to the to the water permeation process substantially similar blood levels of clonidine can be obtained. For example, subjects whose skin resistances are $2.6 \times 10^5$ and $0.44 \times 10^5$ hr atm/cm both will show, after steady state conditions have been achieved, clonidine plasma level of approximately 0.4 ng/ml. The patch described will supply to the skin approximately 3 μg/hr/cm$^2$ of clonidine for 168 hours.

In certain therapeutic regimes it has been suggested that the effectivity of a drug can be improved if periods of therapeutic blood levels are interrupted by drug-free periods. As an example, it has been suggested to interrupt, for varying time periods, the continuous transdermal administration of nitrates such as isosorbide dinitrate or nitroglycerin to prevent or minimize the development of a tolerance to the therapeutic effect of the drug. Typically this has been accomplished by removing a transdermal delivery device and applying another device after a predetermined interval has elapsed. Intervals varying from 1½ hours to 12 hours during daily therapy have been suggested as have longer intervals in multiday nitrate therapy.

One of the advantages of transdermal therapy is the improvement in patient compliance that is obtained from removal of one device and application of a new device at the same time. This advantage is lost when removal and application occur at different times or where onset of a therapeutic effect is desired at an inconvenient time such as during sleep. The devices of this invention are particularly useful in providing a predetermined, delayed onset of therapeutic effect for any desired time period after application to the skin. Thus, a device could be removed and a new one applied simultaneously and the desired drug free interval could still be obtained.

The following examples describe devices according to this invention which could transdermally deliver nitroglycerin over a 24 hour period with onset of therapeutic effect being delayed for different time periods after application.

EXAMPLE 2

An osmotically powered skin patch for delivering nitroglycerin over 18 hours with an initial 6 hour delay is fabricated from a 9 mil thick open-celled foam pad of 50% pore volume, die cut to 3.57 cm diameter. A 2 cm diameter hole is die cut from the center of the foam pad and 10 mil wall thickness polymethylmethacrylate ring of 5 mil height and 2 cm outside diameter is inserted into the hole in the foam pad flush with the bottom of the foam pad. A 2 mil thick semiperimeable membrane comprised of polymethylmethacrylate and cellulose acetate butyrate (50% b tyrate) in a weight ratio of 50:50 is solvent cast from a methylene chloride solution, a 2.5 cm disc of the membrane film is die cut, concentrically positioned over the hole and glued around the edge to the bottom of the foam pad. A 2 mil thick by 2 cm diameter disc of mannitol is compressed and placed inside the well of the foam pad in layered contact with the membrane to provide the osmotic driving force.

Nitroglycerin stabilized onto lactose is formulated to a concentration of 50 mg/ml in a solution of 10% isopropyl alcohol and 90% silicone fluid. The formulation is thickened with 1% Cabosil ® colloidal silicon dioxide and is injected into the hole of the foam pad. Then the foam pad is laminated to a 10 cm$^2$ Medpar impermeable backing with a silicone adhesive thereby completing the manufacture of an osmotically powered nitroglycerin skin patch. The nitroglycerin skin patch will produce a delivery pattern having a delay period of approximately 6 hours from application after which nitroglycerin skin flux will increase rapidly to about 30 $\mu$g/cm$^2$hr for about 18 hours. After 2 hours the patch would be removed and replaced with another device at a fresh skin site. Blood levels will drop to subtherapeutic levels in about 1 hour after removal. Because it takes approximate 2 hours to reach therapeutic blood levels after transdermal delivery commences, the 6 hour delay period will produce an approximately 7 hour period in which sub-therapeutic drug blood levels are observed.

EXAMPLE 3

An osmotically powered nitroglycerin skin patch is constructed as described in Example 2 with the following modifications. Nitroglycerin stabilized onto lactose was formulated to a concentration of approximately 50 mg/ml in an aqueous solution of 30% by weight polyethylene glycol to produce an osmotically active nitroglycerin formulation having an osmotic activity of approximately 39 atmospheres thereby eliminating the need for the monitol layer of Example 2. The nitroglycerin formulation is injected into the well of the foam pad in layered contact with the semipermeable membrane and manufacture of the skin patch is completed as described above. This nitroglycerin skin patch will produce a delivery pattern having a delay of approximately 6 hours after which nitroglycerin skin flux increases rapidly to about 25–30 $\mu$g/cm$^2$hr.

The noval osmotic powered self-regulating skin patch system of this invention enables the high rate delivery of drug for transdermal absorption independent of drug boundary conditions and self-selects the needed skin area for drug transfer, thereby enabling the transdermal application of a wide variety of drugs, including drugs in salt form. While various features of preferred embodiments in the invention have been disclosed and described, it should be apparent that various modifications may be made to the specifically disclosed systems. It is intended that our invention include all such modifications that would be apparent to one skilled in the art and which come within the spirit and scope of the invention and be limited only by the following claims.

We claim:

1. A medical device for delivering a therapeutic agent through an area of skin at a predetermined rate for an extended period of time comprising in combination:
   (a) a fluid impermeable, skin contacting member configured to enclose a predetermined area of skin within its periphery and to form a fluid receiving volume between said member and said area of skin, said predetermined area of skin being selected to be capable of absorbing said agent at a rate greater than said predetermined rate,
   (b) fluid imbibing pump means for delivering therapeutic agent onto said predetermined area of skin upon exposure to an actuating fluid external to said pump means, said pump means establishing said predetermined rate and comprising a housing:
      (i) formed at least in part from actuating fluid permeable material,
      (ii) containing said therapeutic agent, and
      (iii) provided with outlet means for discharging said therapeutic agent and;
   (c) means for maintaining said device on the skin for said extended period of time with said predetermined area of skin confined within said member;

whereby the rate at which said therapeutic agent is delivered to the predetermined area of skin will be lower than the rate at which said predetermined area of skin is capable of absorbing said agent throughout said extended period of time and the rate of delivery of said agent through the skin is maintained at said predetermined rate.

2. The device of claim 1 wherein said fluid permeable portion of said fluid imbibing pump consists of a semipermeable membrane separating said actuating fluid from an osmotic solute therefor, said osmotic solute being present in amounts sufficient to maintain a substantially constant osmotic pressure gradient across said semipermeable membrane throughout a substantial portion of said extended period of time.

3. The device of claim 1 wherein the source of actuating fluid is the skin upon which said device is applied.

4. The device of claim 1 wherein said source of actuating fluid is a chamber within said device adapted to receive a predetermined volume of actuating fluid.

5. The device of claim 3 further comprising an open pore foam disposed within said fluid receiving volume in the path of fluid flow from said outlet means to said predetermined area of skin.

6. The device of claim 4 further comprising an open pore foam disposed within said fluid receiving volume in the path of fluid flow from said outlet means to said predetermined area of skin.

7. The device of claim 5 wherein said open pore foam is impregnated with a material selected from the group consisting of said therapeutic agent, skin permeation enhancers, cytoprotective agents and mixtures thereof.

8. The device of claim 6 wherein said open pore foam is impregnated with a material selected from the group consisting of said therapeutic agent, skin permeation enhancers, cytoprotective agents and mixtures thereof.

9. The device of claim 1 wherein said means for maintaining said device on said skin is a biocompatible adhesive disposed on the skin proximal surface of the periphery of said member.

10. The device of claim 2 wherein said means for maintaining said device on said skin is a biocompatible adhesive disposed on the skin device on said skin is a biocompatible adhesive disposed on the skin proximal surface of the periphery of said member.

11. The device of claim 3 wherein said means for maintaining said device on said skin is a biocompatible adhesive disposed on the skin proximal surface of the periphery of said member.

12. the device of claim 4 wherein said means for maintaining said device on said skin is a biocompatible adhesive disposed on the skin proximal surface fo the periphery of said member.

13. The device of claim 5 wherein said means for maintaining said device on said skin is a biocompatible adhesive disposed on the skin proximal surface of the periphery of said member.

14. the device of claim 6 wherein said means for maintaining said device on said skin is a biocompatible adhesive disposed on the skin proximal surface of the periphery of said member.

15. The device of claim 7 wherein said means for maintaining said device on said skin is a biocompatible adhesive disposed on the skin proximal surface of the periphery of said member.

16. The device of claim 8 wherein said means for maintaining said device on said skin is a biocompatible adhesive disposed on the skin proximal surface of the periphery of said member.

17. The device of claim 1 wherein said means for maintaining said device on the skin is an adhesive overlay.

18. The device of claim 2 wherein said means for maintaining said device on the skin is an adhesive overlay.

19. The device of claim 3 wherein said means for maintaining said device on the skin is an adhesive overlay.

20. The device of claim 4 wherein said means for maintaining said device on the skin is an adhesive overlay.

21. The device of claim 5 wherein said means for maintaining said device on the skin is an adhesive overlay.

22. The device of claim 6 wherein said means for maintaining said device on the skin is an adhesive overlay.

23. The device of claim 7 wherein said means for maintaining said device on the skin is an adhesive overlay.

24. The device of claim 8 wherein said means for maintaining said device on the skin is an adhesive overlay.

25. The device of claim 1 wherein said outlet means comprises a plurality of fluid passageways.

26. The device of claim 5 wherein said outlet means comprises a plurality of fluid passageways.

27. The device of claim 6 wherein said outlet means comprises a plurality of fluid passageways.

28. The device of claim 7 wherein said outlet means comprises a plurality of fluid passageways.

29. The device of claim 8 wherein said outlet means comprises a plurality of fluid passageways.

30. The device of claim 15 wherein said outlet means comprises a plurality of fluid passageways.

31. The device of claim 16 wherein said outlet means comprises a plurality of fluid passageways.

32. The device of claim 23 wherein said outlet means comprises a plurality of fluid passageways.

33. The device of claim 24 wherein said outlet means comprises a plurality of fluid passageways.

34. The device of claim 1 wherein said fluid imbibing pump means delivers said therapeutic agent onto said predetermined area of skin at a rate which is substantially constant throughout said extended period of time.

35. The device of claim 1 wherein said therapeutic agent is contained within said fluid imbibing pump means in admixture with a material selected from the group consisting of permeation enhancers, cytoprotective agents, stabilizing agents and mixtures thereof.

36. The device of claim 2 wherein said therapeutic agent is contained within said fluid imbibing pump means in admixture with a material selected from the group consisting of permeation enhancers, cytoprotective agents, stabilizing agents and mixtures thereof.

37. The device of claim 5 wherein said therapeutic agent is contained within said fluid imbibing pump means in admixture with a material selected from the group consisting of permeation enhancers, cytoprotective agents, stabilizing agents and mixtures thereof.

38. The device of claim 6 wherein said therapeutic agent is contained within said fluid imbibing pump means in admixture with a material selected from the group consisting of permeation enhancers, cytoprotective agents, stabilizing agents and mixtures thereof.

39. The skin patch of claim 7 wherein said therapeutic agent is contained within said fluid imbibing pump means in admixture with a material selected from the group consisting of permeation enhancers, cytoprotective agents, stabilizing agents and mixtures thereof.

* * * * *